United States Patent
Ho et al.

(10) Patent No.: US 11,896,632 B2
(45) Date of Patent: *Feb. 13, 2024

(54) METHODS FOR INHIBITING GROWTH OF ORAL PATHOGENIC BACTERIA AND ALLEVIATING ORAL PATHOGENIC BACTERIA-ASSOCIATED DISORDER

(71) Applicant: GLAC BIOTECH CO., LTD., Tainan (TW)

(72) Inventors: Hsieh-Hsun Ho, Tainan (TW); Yi-Wei Kuo, Tainan (TW); Ching-Wei Chen, Tainan (TW); Wen-Yang Lin, Tainan (TW); Jui-Fen Chen, Tainan (TW); Shu-Hui Chen, Tainan (TW)

(73) Assignee: GLAC BIOTECH CO., LTD., Tainan (TW)

( * ) Notice: Subject to any disclaimer, the term of this patent is extended or adjusted under 35 U.S.C. 154(b) by 0 days.

This patent is subject to a terminal disclaimer.

(21) Appl. No.: 17/573,049

(22) Filed: Jan. 11, 2022

(65) Prior Publication Data

US 2023/0036629 A1 Feb. 2, 2023

(30) Foreign Application Priority Data

Jul. 26, 2021 (CN) .................. 202110843603.8

(51) Int. Cl.
| | | |
|---|---|---|
| *A61K 35/747* | (2015.01) | |
| *A61P 31/04* | (2006.01) | |
| *A61K 8/99* | (2017.01) | |
| *C12N 1/20* | (2006.01) | |
| *C12R 1/225* | (2006.01) | |
| *A61Q 11/00* | (2006.01) | |

(52) U.S. Cl.
CPC ............. *A61K 35/747* (2013.01); *A61K 8/99* (2013.01); *A61P 31/04* (2018.01); *C12N 1/205* (2021.05); *A61Q 11/00* (2013.01); *C12R 2001/225* (2021.05)

(58) Field of Classification Search
CPC ......... A61K 35/747; A61K 8/99; A61P 31/04; C12N 1/205; A61Q 11/00; C12R 2001/225
See application file for complete search history.

(56) References Cited

U.S. PATENT DOCUMENTS

2017/0281698 A1* 10/2017 Chen .................. A61K 8/99

FOREIGN PATENT DOCUMENTS

EP      1634948 A1 * 3/2006 ............. A23G 3/366

* cited by examiner

*Primary Examiner* — Thomas J. Visone
(74) *Attorney, Agent, or Firm* — Hamre, Schumann, Mueller & Larson, P.C.

(57) ABSTRACT

Disclosed herein are methods for inhibiting growth of oral pathogenic bacteria and alleviating an oral pathogenic bacteria-associated disorder using a culture of at least one lactic acid bacterial strain selected from the group consisting of *Lactobacillus rhamnosus* MP108 which is deposited at the China General Microbiological Culture Collection Center (CGMCC) under an accession number CGMCC 21225, and *Lactobacillus paracasei* MP137 which is deposited at the CGMCC under an accession number CGMCC 21224.

8 Claims, No Drawings

METHODS FOR INHIBITING GROWTH OF ORAL PATHOGENIC BACTERIA AND ALLEVIATING ORAL PATHOGENIC BACTERIA-ASSOCIATED DISORDER

CROSS-REFERENCE TO RELATED APPLICATION

This application claims priority of Chinese Invention Patent Application No. 202110843603.8, filed on Jul. 26, 2021.

FIELD

The present disclosure relates to methods for inhibiting growth of oral pathogenic bacteria and alleviating an oral pathogenic bacteria-associated disorder using a culture of at least one lactic acid bacterial strain.

BACKGROUND

Oral pathogenic bacteria are a group of microorganisms that exist on and colonize the surfaces of the human oral cavity, in particular teeth surfaces. Examples of common oral pathogenic bacteria include *Streptococcus mutans*, anaerobic bacteria of *Porphyromonas* spp., *Fusobacterium* spp., and Actinobacteria, etc.

Oral pathogenic bacteria are capable of growing on the surfaces of teeth, gingiva and dental prosthetics (e.g., dentures and bridges), and cause various infectious diseases of the oral cavity. Examples of oral pathogenic bacteria-associated disorders include halitosis, dental caries, dental calculus, and periodontal diseases (including gingivitis and periodontitis).

Conventional methods used for preventing and/or treating infections caused by oral pathogenic bacteria include physical oral cleaning (including tooth brushing, flossing, etc.), use of fluoride toothpaste and antibacterial mouthwash, and antibiotic treatment. However, the effectiveness of such prevention and treatment methods against oral pathogenic bacteria is still not satisfactory, and the main reasons include improper cleaning, and antibiotic resistance exhibited by the oral pathogenic bacteria, as well as serious side effects and adverse effects caused by antibiotics. Therefore, those skilled in the art still strive to develop drugs that can effectively prevent and/or treat infections caused by oral pathogenic bacteria without causing undesirable side effects.

Lactic acid bacteria (LAB) are gram-positive, lactic acid-producing bacteria that are conferred with the generally recognized as safe (GRAS) status, and are widely used as probiotics. Examples of common LAB include *Lactobacillus* spp., *Lactococcus* spp., *Pediococcus* spp., *Streptococcus* spp., *Enterococcus* spp., *Bifidobacterium Bacillus* spp., *Leuconostoc* spp., etc.

Previous studies have demonstrated applications of certain strains of LAB against oral pathogenic bacteria. As reported in Teanpaisan et al. (2011), Lett. App. Microbiol., 53(4):452-459, when different isolates of 10 *Lactobacillus* spp. were tested for their inhibitory activity against oral pathogenic bacteria, certain LAB strains of *Lactobacillus paracasei, Lactobacillus plantarum, Lactobacillus rhamnosus,* and *Lactobacillus casei* demonstrated inhibitory activity against *Streptococcus mutans, Porphyromonas gingivalis* and *Aggregatibacter actinomycetemcomitans*. However, such study showed that a great difference in the capability of inhibiting oral pathogenic bacteria might exist between different isolates of the same LAB species.

As disclosed in Taiwanese Invention Patent No. 1639389 B, isolated *Lactobacillus acidophilus* F-1, *Lactobacillus salivarius* AP-32, *Lactobacillus reuteri* GL-104, *Lactobacillus paracasei* GL-156, *Lactobacillus paracasei* ET-66, *Lactobacillus helveticus* RE-78, and *Lactobacillus rhamnosus* CT-53 exhibit discrepancy in inhibitory activity against different oral pathogenic bacteria. For example, *Lactobacillus paracasei* GL-156 has inhibitory activity of up to 96.93% against *Fusobacterium nucleatum* subsp. *polymorphum*, but shows no inhibitory effect on *Streptococcus mutans*.

In spite of the aforesaid, there is still a need to develop a new strategy that can be utilized for inhibiting different oral pathogenic bacteria and exhibiting satisfactory effect in alleviating diseases associated with oral pathogenic bacteria.

SUMMARY

Therefore, in a first aspect, the present disclosure provides a method for inhibiting growth of oral pathogenic bacteria which can alleviate at least one of the drawbacks of the prior art.

The method includes applying a composition including a culture of at least one lactic acid bacterial strain onto an object. The at least one lactic acid bacterial strain is selected from the group consisting of *Lactobacillus rhamnosus* MP108 which is deposited at the China General Microbiological Culture Collection Center (CGMCC) under an accession number CGMCC 21225, and *Lactobacillus paracasei* MP137 which is deposited at the CGMCC under an accession number CGMCC 21224.

In a second aspect, the present disclosure provides a method for alleviating an oral pathogenic bacteria-associated disorder, which can alleviate at least one of the drawbacks of the prior art, and which includes administering to a subject in need thereof the aforesaid composition.

DETAILED DESCRIPTION

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this disclosure belongs. One skilled in the art will recognize many methods and materials similar or equivalent to those described herein, which could be used in the practice of this disclosure. Indeed, this disclosure is in no way limited to the methods and materials described.

In the development of methods for inhibiting the growth of oral pathogenic bacteria, the applicant surprisingly found that a culture of certain lactic acid bacterial strains exhibits an inhibitory effect on oral pathogenic bacteria.

Therefore, the present disclosure provides a method for inhibiting growth of oral pathogenic bacteria, which includes applying a composition including a culture of at least one lactic acid bacterial strain onto an object.

The at least one lactic acid bacterial strain is selected from the group consisting of *Lactobacillus rhamnosus* MP108 which is deposited at the China General Microbiological Culture Collection Center (CGMCC) under an accession number CGMCC 21225, and *Lactobacillus paracasei* MP137 which is deposited at the CGMCC under an accession number CGMCC 21224.

According to the present disclosure, the oral pathogenic bacteria are selected from the group consisting of *Streptococcus mutans, Porphyromonas gingivalis, Fusobacterium nucleatum* subsp. *polymorphum, Aggregatibacter actinomycetemcomitans, Treponema denticola, Prevotella intermedia, Parvimonas micra, Campylobacter rectus, Eikenella corrodens*, and combinations thereof.

According to the present disclosure, the culture of the lactic acid bacterial strain may be prepared by culturing the abovementioned lactic acid bacterial strain in an amount ranging from $1\times10^6$ CFU/mL to $1\times10^{10}$ CFU/ml, in a culture medium suitable for growth thereof. In certain embodiments, the abovementioned lactic acid bacterial strain is cultivated in an amount ranging from $1\times10^7$ CFU/mL to $1\times10^9$ CFU/mL in a culture medium suitable for growth thereof.

As used herein, the term "culturing" can be used interchangeably with other terms such as "fermentation" and "cultivation".

It should be noted that the procedures and operating conditions for culturing the lactic acid bacterial strain may be adjusted according to practical requirements. In this regard, those skilled in the art may refer to journal articles, e.g., Hsieh P. S. et al. (2013), *New Microbiol.*, 36:167-179.

According to the present disclosure, the culture medium used for culturing the lactic acid bacterial strain may be purchased commercially or self-prepared using standard techniques well known to those skilled in the art. Examples of the culture medium may include, but are not limited to, MRS (De Man, Rogosa and Sharpe) broth and MRS broth supplemented with cysteine. In an exemplary embodiment, the culture medium is BD Difco™ Lactobacilli MRS broth, i.e., MRS broth purchased commercially from BD (Becton, Dickinson and Company) Biosciences which is supplemented with cysteine (Manufacturer: BD Biosciences; Catalogue no.: 288130).

According to the present disclosure, the culture of the lactic acid bacterial strain is a liquid culture.

According to the present disclosure, the liquid culture may have a bacterial concentration ranging from $1\times10^6$ CFU/mL to $1\times10^{10}$ CFU/mL. In an exemplary embodiment, the liquid culture has a bacterial concentration of $1\times10^9$ CFU/mL.

According to the present disclosure, the composition may include the liquid cultures of *Lactobacillus rhamnosus* MP108 and *Lactobacillus paracasei* MP137.

In certain embodiments, a ratio of a number of *Lactobacillus rhamnosus* MP108 to that of *Lactobacillus paracasei* MP137 in the composition ranges from 1:0.43 to 1:2.33. In an exemplary embodiment, the ratio of the number of *Lactobacillus rhamnosus* MP108 to that of *Lactobacillus paracasei* MP137 in the composition is 1:1.

According to the present disclosure, the culture (which may be a liquid culture) of the lactic acid bacterial strain may be heat-inactivated.

It should be noted that the procedures and operating conditions for performing heat-inactivation may be adjusted according to practical requirements. In this regard, those skilled in the art may refer to journal articles, e.g., Chen, Y. T. et al. (2020), *Lett. Appl. Microbiol.*, 70(4):310-317.

According to the present disclosure, the culture (which may be a liquid culture) of the lactic acid bacterial strain may be heat-inactivated at a temperature of 100° C. for a time period ranging from 30 minutes to 1 hour. In an exemplary embodiment, the culture (which may be a liquid culture) of the lactic acid bacterial strain is heat-inactivated at a temperature of 100° C. for 1 hour.

According to the present disclosure, the liquid culture of the lactic acid bacterial strain may be subjected to a solid-liquid separation treatment, and is substantially free of bacterial cells.

In certain embodiments, when the liquid cultures of *Lactobacillus rhamnosus* MP108 and *Lactobacillus paracasei* MP137 are substantially free of bacterial cells, a volume ratio of the liquid cultures of *Lactobacillus rhamnosus* MP108 and *Lactobacillus paracasei* MP137 in the composition ranges from 1:0.43 to 1:2.33. In an exemplary embodiment, the volume ratio of the liquid cultures of *Lactobacillus rhamnosus* MP108 and *Lactobacillus paracasei* MP137 in the composition is 1:1.

As used herein, the term "substantially free of" means that the liquid culture lacks a significant amount of a specified component (i.e., bacterial cells). In certain embodiments, the amount of the bacterial cells does not have a measurable effect on the properties of the liquid culture. In other embodiments, the liquid culture is completely free of bacterial cells.

According to the present disclosure, the solid-liquid separation treatment may be selected from the group consisting of a centrifugation treatment (e.g., a multi-stage centrifugation treatment), a filtration treatment, a solid-liquid separator treatment, and combinations thereof. In an exemplary embodiment, the solid-liquid separation treatment is a centrifugation treatment.

Examples of the object may include, but are not limited to, medical devices, medical instruments, food preparation countertops, food packaging countertops, production countertops, consumer products, water treatment systems, and water delivery systems.

In certain embodiments, the object may be selected from the group consisting of dentures, mouth guards, dairy product lines, water pipes, adhesive bandages, components of water treatment equipment, medical instruments, dental instruments, food industry processing equipment, hospital beds and tables, animal feeding trays, washing machines, dishwashers, towels, plates, trays, bowls, utensils, cups, glassware, cutting boards, plate draining racks, sinks, toilets, toilet seats, food and beverage production lines, food storage containers, beverage storage containers, forks, knives, and spoons.

Since *Lactobacillus rhamnosus* MP108 and *Lactobacillus paracasei* MP137 have been verified to effectively inhibit the growth of oral pathogenic bacteria, the applicant believes that *Lactobacillus rhamnosus* MP108 and *Lactobacillus paracasei* MP137 have a high potential for alleviating disorders associated with oral pathogenic bacteria.

Therefore, the present disclosure provides a method for alleviating an oral pathogenic bacteria-associated disorder, which includes administering to a subject in need thereof the aforesaid composition.

Examples of the oral pathogenic bacteria-associated disorder may include, but are not limited to, halitosis, dental caries, gingivitis, acute necrotizing ulcerative gingivitis (ANUG) (also known as trench mouth or Vincent's disease), and periodontitis.

As used herein, the term "alleviating" or "alleviation" refers to at least partially reducing, ameliorating, relieving, controlling, treating or eliminating one or more clinical signs of an oral pathogenic bacteria-associated disorder; and lowering, delaying, stopping or reversing the progression of severity regarding the condition or symptom of an oral pathogenic bacteria-associated disorder being treated.

According to the present disclosure, alleviation of the oral pathogenic bacteria-associated disorder may involve at least one of inhibiting growth of the oral pathogenic bacteria, inhibiting colonization of the oral pathogenic bacteria, and inhibiting biofilm formation of the oral pathogenic bacteria.

According to the present disclosure, the composition may be formulated as a food product using a standard technique well known to one of ordinary skill in the art. For example, the composition may be directly added to an edible material as a food additive, or may be used to prepare an intermediate composition (e.g., a premix) suitable to be subsequently added to the edible material.

As used herein, the term "food product" refers to any article or substance that can be ingested by a subject into the body thereof. Examples of the food product may include, but are not limited to, milk powder, fermented milk, yogurt, butter, beverages (e.g., tea, coffee, etc.), functional beverages, flour products, baked foods, confectionery, candies, fermented foods, animal feeds, health foods, infant foods, and dietary supplements.

According to the present disclosure, the composition may be formulated as an oral hygiene composition for preparing an oral hygiene product using a standard technique well known to one of ordinary skill in the art. For example, the oral hygiene composition may be added to an oral hygiene material as an additive, or may be used to prepare an intermediate composition (e.g., a premix) suitable to be subsequently added to the oral hygiene material.

Examples of the oral hygiene product may include, but are not limited to, mouthwash, mouth rinse, dental soak, dental pastes, dentifrices, dental powders, dental gels, oral sprays, chewing tablets, chewing gums, lozenges, buccal tablets, dental floss, dental tapes, and toothpicks.

According to the present disclosure, the composition may be formulated as a pharmaceutical composition. The pharmaceutical composition may further include a pharmaceutically acceptable carrier, and may be made into a dosage form suitable for parenteral administration, oral administration or topical administration using technology well-known to those skilled in the art.

Examples of the pharmaceutically acceptable carrier may include, but are not limited to, solvents, buffers, emulsifiers, suspending agents, decomposers, disintegrating agents, dispersing agents, binding agents, excipients, stabilizing agents, chelating agents, diluents, gelling agents, preservatives, wetting agents, lubricants, absorption delaying agents, liposomes, and the like. The choice and amount of the pharmaceutically acceptable carrier are within the expertise of those skilled in the art.

In certain embodiments, the pharmaceutical composition may be formulated into a sublingual dosage form suitable for parenteral administration. Examples of the sublingual dosage form may include, but are not limited to, tablets, wafers, films, and patches.

Examples of the dosage form for oral administration include, but are not limited to, sterile powders, tablets, troches, sustained film-coated tablets, oral ointments, pellets, capsules, dispersible powders or granules, solutions, suspensions, emulsions, drops, syrup, elixirs, slurry, sprays, and the like.

Examples of the dosage form for topical administration to the skin or mucous membrane (i.e., manufactured as an external preparation) include, but are not limited to, emulsions, gels, ointments, creams, patches, liniments, powders, aerosols, sprays, lotions, serums, pastes, foams, drops, suspensions, salves, and bandages.

As used herein, the term "administering" or "administration" means introducing, providing or delivering a predetermined active ingredient to a subject by any suitable routes to perform its intended function.

As used herein, the term "subject" refers to any animal of interest, such as humans, monkeys, cows, sheep, horses, pigs, goats, dogs, cats, mice, and rats. In certain embodiments, the subject is a human.

The dose and frequency of administration of the composition of the present disclosure may vary depending on the following factors: the severity of the illness or disorder to be treated, routes of administration, and weight, age, physical condition and response of the subject to be treated. In general, the composition may be administered in a single dose or in several doses.

The present disclosure will be further described by way of the following examples. However, it should be understood that the following examples are intended solely for the purpose of illustration and should not be construed as limiting the present disclosure in practice.

EXAMPLES

General Experimental Materials:
1. Lactic Acid Bacterial (LAB) Strain
A. *Lactobacillus rhamnosus* MP108

*Lactobacillus rhamnosus* MP108, which is disclosed in CN 102604854 B and is readily available to the public, has been deposited at the Deutsche Sammlung von Mikroorganismen and Zellkulturen (DSMZ) GmbH (Inhoffenstraße 7B, 38124 Braunschweig, Germany) under an accession number DSM 24229 since Nov. 19, 2010 in accordance with the Budapest Treaty. *Lactobacillus rhamnosus* MP108 has also been deposited at the China General Microbiological Culture Collection Center (CGMCC) of Chinese Academy of Sciences, the Institute of Microbiology (No. 1, West Beichen Rd., Chaoyang District, Beijing 100101, China) under an accession number CGMCC 21225 since Nov. 23, 2020 by the applicant.

B. *Lactobacillus paracasei* MP137

*Lactobacillus paracasei* MP137, which is disclosed in CN 102604854 B and is readily available to the public, has been deposited at the DSMZ GmbH under an accession number DSM 24230 since Nov. 10, 2010 in accordance with the Budapest Treaty. *Lactobacillus rhamnosus* MP137 has also been deposited at the CGMCC under an accession number CGMCC 21224 since Nov. 23, 2020 by the applicant.

C. Comparative LAB Strains

The applicant isolated the following LAB strains using procedures described in Hsu Y. J. et al. (2018), Nutrients, 10(7):862 to serve as comparative LAB strains: *Lactobacillus rhamnosus* L-68 isolated from the breast milk of a healthy subject, and *Lactobacillus paracasei* L-30 isolated from the feces of another healthy subject.

2. Oral Pathogenic Bacterial Strains

The oral pathogenic bacterial strains used in the following experiments are readily available to the public, and were purchased from the Bioresource Collection and Research Center (BCRC) of the Food Industry Research and Development Institute (FIRDI) (No. 331, Shih-Pin Rd., Hsinchu City 300, Taiwan). The relevant information regarding each of the oral pathogenic bacterial strains (including scientific name, and BCRC accession number and corresponding American Type Culture Collection (ATCC) accession number (if any)) is listed in Table 1 below.

TABLE 1

| Oral pathogenic bacterial strains | Accession number |
| --- | --- |
| Streptococcus mutans | BCRC 10793T (corresponding to ATCC 25175) |
| Porphyromonas gingivalis | BCRC 17688 |
| Fusobacterium nucleatum subsp. polymorphum | BCRC 17679 (corresponding to ATCC 10953) |
| Aggregatibacter actinomycetemconitans | BCRC 14405 (corresponding to ATCC 29522) |

General Experimental Procedures:

1. Preparation of Liquid Culture of LAB Strain

A respective one of the four LAB strains described in section 1 of the General Experimental Materials was inoculated into 5 mL of a BD Difco™ Lactobacilli MRS (De Man, Rogosa and Sharpe) broth (Catalogue no.: 288130) supplemented with 0.05% (w/w) cysteine, and was then cultured in an incubator (37° C., 5% $CO_2$) for 24 hours, so as to obtain a liquid culture of the respective LAB strain. The bacterial concentration was adjusted to 1×10 CFU/mL using a MRS broth.

2. Preparation of Liquid Culture of Oral Pathogenic Bacterial Strain

A respective one of the four oral pathogenic bacterial strains described in section 2 of the General Experimental Materials was activated by culturing using the culture medium and culture conditions described in Table 2 below, thereby obtaining a liquid culture of the respective oral pathogenic bacterial strain having a bacterial concentration ranging from $1\times10^7$ CFU/ml, to $1\times10^9$ CFU/mL.

TABLE 2

| Oral pathogenic bacterial strains | Culture medium (Manufacturer; Catalogue no.) | Culture conditions |
| --- | --- | --- |
| Streptococcus mutans | Tryptic soy broth (TSB) (Thermo Fisher Scientific; R112996) | 37° C., 5% $CO_2$, 20 hours |
| Porphyromonas gingivalis | TSB (Thermo Fisher Scientific; R112996) supplemented with BBL ™ 5% sheep blood (BD Biosciences; 211946) | 37° C., semi-anaerobic, 72 hours |
| Fusobacterium nucleatum subsp. polymorphum | TSB (Thermo Fisher Scientific; R112996) supplemented with BBL ™ 5% sheep blood (BD Biosciences; 211946) | 37° C., semi-anaerobic, 72 hours |
| Aggregatibacter actinomycetemcomitans | Remel ™ brain heart infusion (BHI) broth (Thermo Fisher Scientific; R452472) supplemented with BBL ™ 5% sheep blood (BD Biosciences; 211946) | 37° C., semi-anaerobic, 72 hours |

3. Statistical Analysis

All the experiments described below were performed in triplicates. The experimental data of all the test groups are expressed as mean.

Example 1. Evaluation of the Effect of Liquid Culture of Lactic Acid Bacterial (LAB) Strain on Inhibition of Oral Pathogenic Bacterial Strain In order to evaluate the efficacy of liquid cultures of certain lactic acid bacterial strains on the inhibition of certain oral pathogenic bacterial strains, the following experiments were conducted.

Experimental Materials:

1. MRS Agar Plate

The MRS agar plate used in the following experiments was prepared by adding agar powder (1.5% w/v) (Manufacturer: Neogen Corporation; Catalogue no.: NCM0214A) into a BD Difco™ Lactobacilli MRS broth (Catalogue no.: 288130) and using techniques well-known to those skilled in the art.

2. Top Agar Medium

Agar powder (1.5% w/v) described in section 1 above was added to a respective one of the tryptic soy broth (TSB), TSB supplemented with BB™ 5% sheep blood, and Remel™ brain heart infusion (BHI) broth supplemented with BBL™ 5% sheep blood as described in section 2 of the General Experimental Procedures, followed by performing a sterilization process at 121° C. for 15 minutes to obtain a respective one of melted TSB agar medium, melted TSB agar medium supplemented with BBL™ 5% sheep blood, and melted Remel™ PHI agar medium supplemented with BBL™ 5% sheep blood, which was then placed into a water bath having a temperature of 45° C., so as to be used as a top agar medium in the following experiments.

Experimental Procedures:

The double agar overlay assay was performed according to the procedures and conditions disclosed in Chen, Y. T. et al. (2020), Lett. Appl. Microbiol., 70(4): 310-317.

First, each of the four liquid cultures of LAB strains described in section 1 of the General Experimental Procedures served as a LAB single liquid culture group, i.e., a corresponding one of LAB single liquid culture experimental groups 1 and 2 (abbreviated as LAB single liquid culture EG1 and EG2) and LAB single liquid culture comparative groups 1 and 2 (abbreviated as LAB single liquid cultures CG1 and CG2), as shown in Table 3 below. In addition, the liquid culture of Lactobacillus rhamnosus MP108 was mixed with the liquid culture of Lactobacillus paracasei MP137 at a specified volume ratio of Lactobacillus rhamnosus MP108 to Lactobacillus paracasei MP137 so as to obtain five liquid culture mixtures each serving as a LAB liquid culture mixture experimental group, i.e., a corresponding one of LAB liquid culture mixture experimental groups 1 to 5 (abbreviated as LAB liquid culture mixture EG1 to EG5), as shown in Table 4. The liquid culture of each group had a total bacterial concentration of $10^9$ CFU/mL.

TABLE 3

| Group | LAB strain |
| --- | --- |
| LAB single liquid culture EG1 | Lactobacillus rhamnosus MP108 |
| LAB single liquid culture EG2 | Lactobacillus paracasei MP137 |
| LAB single liquid culture CG1 | Lactobacillus rhamnosus L-68 |
| LAB single liquid culture CG2 | Lactobacillus paracasei L-30 |

TABLE 4

| Group | Volume ratio of *Lactobacillus rhamnosus* MP108 to *Lactobacillus paracasei* MP137 |
|---|---|
| LAB liquid culture mixture EG1 | 1:0.11 |
| LAB liquid culture mixture EG2 | 1:0.43 |
| LAB liquid culture mixture EG3 | 1:1 |
| LAB liquid culture mixture EG4 | 1:2.33 |
| LAB liquid culture mixture EG5 | 1:9 |

After that, a sterilized cotton swab was dipped into the liquid culture of the respective group (approximately 1 mL) to collect the same, and then a 2 cm-wide line was streaked using the cotton swab with the liquid culture along a diameter of an MRS agar plate as described in section 1 of the Experimental Materials, followed by culturing at 37° C. under a semi-anaerobic condition for 48 hours, so that the LAB strain in the respective group formed a growth zone with a width of approximately 2 cm on the MRS agar medium. Moreover, MRS broth not inoculated with any of the aforesaid LAB strain was likewise collected to streak a line on an MRS agar plate as described in section 1 of the Experimental Materials to serve as a blank control group (BCG), followed by the same processes.

The melted TSB agar medium (serving as a top agar medium) as described in section 2 of the Experimental Materials was poured onto the MRS agar plate of the respective group, so that the MRS agar medium was overlaid with the melted TSB agar medium. After solidification of the TSB agar medium to form a double layer agar (DLA) medium, a sterilized cotton swab was dipped into the liquid culture of *Streptococcus mutans* described in section 2 of the General Experimental Procedures to collect the same, and then the collected liquid culture of *Streptococcus mutans* was evenly spread on the surface of the DLA medium (i.e., on the top agar medium), followed by incubation in an incubator at 37° C. and 5% $CO_2$ for 48 hours. The efficacy of the liquid culture of each group in inhibiting the growth of *Streptococcus mutans* was evaluated by measuring the width of inhibition zone formed on the surface of the DLA medium.

The inhibitory effect of the liquid culture of each group on *Porphyromonas gingivalis*, *Fusobacterium nucleatum* subsp. *polymorphum*, and *Aggregatibacter Actinomycetemcomitans* was evaluated with reference to the abovementioned procedures and conditions used for *Streptococcus mutans*, except that the DLA medium containing the TSB agar medium supplemented with BBL™ 5% sheep blood as a top agar medium was used for evaluating the effect of the liquid culture of each group on *Porphyromonas gingivalis* and *Fusobacterium nucleatum subsp. polymorphum*, while the DLA medium containing the Remel™ BHI agar medium supplemented with BBL™ 5% sheep blood as a top agar medium was used for evaluating the effect of the liquid culture of each group on *Aggregatibacter Actinomycetemcomitans*. The experimental data were analyzed according to the procedures described in section 3 of the General Experimental Procedures.

Results:

The width of the inhibition zone formed after application of the liquid culture of each group against a respective one of the four oral pathogenic bacterial strains is shown in Table 5 below.

TABLE 5

| | Width of inhibition zone (cm) | | | |
|---|---|---|---|---|
| Group | *Streptococcus mutans* | *Porphyromonas gingivalis* | *Fusobacterium nucleatum* subsp. *polymorphum* | *Aggregatibacter actinomycetemcomitans* |
| Blank control group | 0.0 | 0.0 | 0.0 | 0.0 |
| LAB single liquid culture EG1 | 4.0 | 3.1 | 3.0 | 3.5 |
| LAB single liquid culture EG2 | 3.5 | 2.5 | 3.1 | 3.4 |
| LAB single liquid culture CG1 | 2.1 | 2.3 | 2.2 | 2.0 |
| LAB single liquid culture CG2 | 2.3 | 2.2 | 2.1 | 2.3 |
| LAB liquid culture mixture EG1 | 4.2 | 3.2 | 3.2 | 3.3 |
| LAB liquid culture mixture EG2 | 4.3 | 3.4 | 3.6 | 3.9 |
| LAB liquid culture mixture EG3 | 5.5 | 4.0 | 3.9 | 4.3 |
| LAB liquid culture mixture EG4 | 4.4 | 3.7 | 3.6 | 4.1 |
| LAB liquid culture mixture EG5 | 4.1 | 3.2 | 3.1 | 3.4 |

As shown in Table 5, an inhibition zone that is significant in size against a respective one of the four oral pathogenic bacterial strains was formed by each of LAB single liquid culture EG1 and EG2 and LAB liquid culture mixture EG1 to EG5, and the width of the inhibition zone formed by each of the LAB single liquid culture EG1 and EG2 was significantly greater than those formed by the LAB single liquid culture CG1 and CG2. These results indicate that the liquid culture of Lactobacillus rhamnosus MP108 and liquid culture of Lactobacillus paracasei MP137 are capable of effectively inhibiting the growth of oral pathogenic bacteria, and such inhibitory effect is significantly greater that those shown by different isolates of the same LAB species (i.e., Lactobacillus rhamnosus L-68 and Lactobacillus paracasei L-30).

Moreover, in comparison with the LAB single liquid culture EG1 and EG2, the inhibition zone formed by the LAB liquid culture mixture EG2 to EG4 generally showed a trend of increase in width, with the LAB liquid culture mixture EG3 showing a most significant increase in width in particular. This results suggest that the liquid culture of Lactobacillus rhamnosus MP108 and liquid culture of Lactobacillus paracasei MP137, when mixed in a specified volume ratio, exhibit a synergistic effect on inhibiting the growth of oral pathogenic bacteria.

Example 2. Evaluation of the Effect of Cell Culture Supernatant of LAB Strain on Inhibition of Oral Pathogenic Bacterial Strain In order to evaluate the efficacy of cell culture supernatants of certain lactic acid bacterial strains on the growth inhibition of certain oral pathogenic bacterial strains, the following experiments were conducted.

Experimental Procedures:

A. Preparation of Cell Culture Supernatant of LAB Strain

A respective one of the four liquid cultures of LAB strains described in section 1 of the General Experimental Procedures was subjected to centrifugation at 4° C. under a speed of 4000 rpm for 10 minutes to form cell culture supernatant and pellet fractions. The resultant cell culture supernatants of LAB strains were collected to be used in the following experiments.

B. Co-Cultivation of Cell Culture Supernatant of LAB Strain with Oral Pathogenic Bacterial Strain Each of the four cell culture supernatants of LAB strains as described in section A above served as a LAB single cell culture supernatant group, i.e., a corresponding one of LAB single cell culture supernatant experimental groups 1 and 2 (abbreviated as LAB single cell culture supernatant EG1 and EG2) and LAB single cell culture supernatant comparative groups 1 and 2 (abbreviated as LAB single cell culture supernatant CG1 and CG2), as shown in Table 6 below. In addition, the cell culture supernatant of Lactobacillus rhamnosus MP108 was mixed with the cell culture supernatant of Lactobacillus paracasei MP137 at a specified volume ratio so as to obtain five cell culture supernatant mixtures each serving as a LAB cell culture supernatant mixture experimental group, i.e., a corresponding one of LAB cell culture supernatant mixtures experimental groups 1 to 5 (abbreviated as LAB cell culture supernatant mixture EG1 to EG5), as shown in Table 7 below.

TABLE 6

| Group | LAB strain |
| --- | --- |
| LAB single cell culture supernatant EG1 | Lactobacillus rhamnosus MP108 |

TABLE 6-continued

| Group | LAB strain |
| --- | --- |
| LAB single cell culture supernatant EG2 | Lactobacillus paracasei MP137 |
| LAB single cell culture supernatant CG1 | Lactobacillus rhamnosus L-68 |
| LAB single cell culture supernatant CG2 | Lactobacillus paracasei L-30 |

TABLE 7

| Group | Volume ratio of Lactobacillus rhamnosus MP108 to Lactobacillus paracasei MP137 |
| --- | --- |
| LAB cell culture supernatant mixture EG1 | 1:0.11 |
| LAB cell culture supernatant mixture EG2 | 1:0.43 |
| LAB cell culture supernatant mixture EG3 | 1:1 |
| LAB cell culture supernatant mixture EG4 | 1:2.33 |
| LAB cell culture supernatant mixture EG5 | 1:9 |

The aforesaid cell culture supernatant (100 μL) of the respective group was added to 4.8 mL of a TSB medium. A blank control group (BCG) was prepared by adding 100 μL of LAB strain-free MRS broth to 4.8 mL of a TSB medium. Thereafter, 100 μL of a liquid culture of Streptococcus mutans as described in section 2 of the General Experimental Procedures, which had a bacterial concentration of $1\times10^7$ CFU/mL, was added to the cell culture supernatant of the respective group, followed by incubation in an incubator at 37° C. and 5% $CO_2$ for 20 hours, thereby obtaining a co-culture product.

In addition, co-cultivation of a respective one of Porphyromonas gingivalis, Fusobacterium nucleatum subsp. polymorphum, and Aggregatibacter Actinomycetemcomitans with the cell culture supernatant of each group was performed according to the abovementioned procedures and conditions used for Streptococcus mutans, except that: TSB supplemented with BBL™ 5% sheep blood was used for culturing Porphyromonas gingivalis and Fusobacterium nucleatum subsp. polymorphum, while Remel™ PHI broth supplemented with BBL™ 5% sheep blood was used for culturing Aggregatibacter Actinomycetemcomitans; and the incubation was performed at a time period ranging from 48 hours to 72 hours.

C. Determination of Percentage of Growth Inhibition

The respective co-culture product obtained in section B above was subjected to ten-fold serial dilution using an appropriate culture medium as described in Table 2 of section 2 of the General Experimental Procedures according to the type of oral pathogenic bacterial strains used for co-cultivation, thereby obtaining ten dilutions having a dilution factor ranging from $10^1$ to $10^{10}$. Next, 100 μL of a respective one of the ten dilutions was evenly spread on a DLA medium having an appropriate top agar medium depending on the type of oral pathogenic bacterial strains, as described in the Experimental Procedures of Example 1, followed by incubation in an incubator at 37° C. and 5% $CO_2$ for a time period ranging from 48 hours to 72 hours. Thereafter, for each co-culture product, a proper dilution factor was chosen for determining the number of oral pathogenic bacterial colonies formed on the top agar medium.

The growth inhibition percentage of a respective one of the four oral pathogenic bacterial strains regarding each group was calculated by substituting the thus determined number of colonies into the following formula (1):

$$A=(B-C)/B\times100 \tag{1}$$

where A=growth inhibition percentage (%)
B=number of colonies of the oral pathogenic bacterial strain regarding the blank control group
C=number of colonies of the oral pathogenic bacterial strain regarding the respective group The data thus obtained were analyzed according to the procedures as described in section 3 of the General Experimental Procedures.

Results:

The growth inhibition percentage of a respective one of the four oral pathogenic bacterial strains regarding each group is shown in Table 8 below.

TABLE 8

| | Growth inhibition percentage (%) | | | |
|---|---|---|---|---|
| Group | Streptococcus mutans | Porphyromonas gingivalis | Fusobacterium nucleatum subsp. polymorphum | Aggregatibacter actinomycetemcomitans |
| Blank control group | 0.00 | 0.00 | 0.00 | 0.00 |
| LAB single cell culture supernatant EG1 | 70.23 | 82.46 | 71.56 | 81.09 |
| LAB single cell culture supernatant EG2 | 71.56 | 88.46 | 76.54 | 83.79 |
| LAB single cell culture supernatant CG1 | 51.23 | 49.81 | 41.32 | 44.43 |
| LAB single cell culture supernatant CG2 | 52.71 | 41.85 | 49.81 | 51.07 |
| LAB cell culture supernatant mixture EG1 | 74.16 | 89.54 | 77.81 | 81.54 |
| LAB cell culture supernatant mixture EG2 | 81.23 | 89.06 | 83.13 | 84.33 |
| LAB cell culture supernatant mixture EG3 | 96.19 | 90.56 | 92.23 | 92.88 |
| LAB cell culture supernatant mixture EG4 | 85.64 | 87.42 | 80.46 | 87.44 |
| LAB cell culture supernatant mixture EG5 | 73.13 | 85.12 | 73.85 | 82.55 |

As shown in Table 8, each of the LAB single cell culture supernatant EG1 and EG2 and the LAB cell culture supernatant mixture EG1 to EG5 exhibited a significant growth inhibitory effect on each of the oral pathogenic bacterial strains, and the percentage of growth inhibition exhibited by each of the LAB single cell culture supernatant EG1 and EG2 was significantly higher compared with that of the LAB single cell culture supernatant CG1 and CG2. These results indicate that the cell culture supernatant of *Lactobacillus rhamnosus* MP108 and the cell culture supernatant of *Lactobacillus paracasei* MP137 are capable of effectively inhibiting the growth of oral pathogenic bacteria, and such inhibitory effect is significantly greater that those shown by different isolates of the same LAB species (i.e., *Lactobacillus rhamnosus* L-68 and *Lactobacillus paracasei* L-30).

In addition, in comparison with the LAB single cell culture supernatant EG1 and EG2, the LAB cell culture supernatant mixture EG2 to EG4 generally showed a trend of increase in growth inhibition percentage, with the LAB cell culture supernatant mixture EG3 showing a most significant increase in growth inhibition percentage in particular. These results suggest that, the cell culture supernatant of *Lactobacillus rhamnosus* MP108 and the cell culture supernatant of *Lactobacillus paracasei* MP137, when mixed in a specified volume ratio, exhibit a synergistic effect in inhibiting the growth of oral pathogenic bacteria.

Example 3. Evaluation of the Effect of Heat-Inactivated Liquid Culture of LAB Strain on Inhibition of Oral Pathogenic Bacterial Strain In order to evaluate the efficacy of heat-inactivated liquid cultures of certain lactic acid bacterial strains on the growth inhibition of certain oral pathogenic bacterial strains, the following experiments were conducted.

Experimental Procedures:

A. Preparation of Heat-Inactivated Liquid Culture of LAB Strain

A respective one of the four liquid cultures of LAB strains described in section 1 of the General Experimental Procedures was heated at 100° C. for 1 hour, thereby obtaining a heat-inactivated liquid culture of the respective LAB strain (still having a bacterial concentration of $1\times10^9$ CFU/mL) to be used in the following experiments.

B. Co-Cultivation of Heat-Inactivated Liquid Culture of LAB Strain with Oral Pathogenic Bacterial Strain Each of the four heat-inactivated liquid cultures of LAB strains as described in section A above served as a LAB single heat-inactivated liquid culture group, i.e., a corresponding one of LAB single heat-inactivated liquid culture experimental groups 1 and 2 (abbreviated as LAB single heat-inactivated liquid culture EG1 and EG2) and LAB single heat-inactivated liquid culture comparative groups 1 and (abbreviated as LAB single heat-inactivated liquid culture CG1 and CG2), as shown in Table 9 below. In addition, the heat-inactivated liquid culture of *Lactobacillus rhamnosus* MP108 was mixed with the heat-inactivated liquid culture of *Lactobacillus paracasei* MP137 at a specified volume ratio so as to obtain five heat-inactivated liquid culture mixtures each serving as a LAB heat-inactivated liquid culture mixture experimental group, i.e., a corresponding one of LAB heat-inactivated liquid culture mixture experimental groups 1 to 5 (abbreviated as LAB heat-inactivated liquid culture mixture EG1 to EG5), as shown in Table 10 below.

TABLE 9

| Group | LAB strain |
| --- | --- |
| LAB single heat-inactivated liquid culture EG1 | *Lactobacillus rhamnosus* MP108 |
| LAB single heat-inactivated liquid culture EG2 | *Lactobacillus paracasei* MP137 |
| LAB single heat-inactivated liquid culture CG1 | *Lactobacillus rhamnosus* L-68 |
| LAB single heat-inactivated liquid culture CG2 | *Lactobacillus paracasei* L-30 |

TABLE 10

| Group | Volume ratio of *Lactobacillus rhamnosus* MP108 to *Lactobacillus paracasei* MP137 |
| --- | --- |
| LAB heat-inactivated liquid culture mixture EG1 | 1:0.11 |
| LAB heat-inactivated liquid culture mixture EG2 | 1:0.43 |
| LAB heat-inactivated liquid culture mixture EG3 | 1:1 |
| LAB heat-inactivated liquid culture mixture EG4 | 1:2.33 |
| LAB heat-inactivated liquid culture mixture EG5 | 1:9 |

The heat-inactivated liquid culture of each group was subjected to co-cultivation with a respective one of the four oral pathogenic bacterial strains according to the procedures and conditions as described in section B of Example 2, so as to obtain a co-culture product.

C. Determination of Growth Inhibition Percentage

The respective co-culture product obtained in section B above was subjected to determination of growth inhibition percentage according to the procedures and conditions as described in section C of Example 2, and the data thus obtained were analyzed according to the procedures described in section 3 of the General Experimental Procedures.

Results:

The percentage of growth inhibition of a respective one of the four oral pathogenic bacterial strain regarding each group is shown in Table 11 below.

TABLE 11

| | Growth inhibition percentage (%) | | | |
| --- | --- | --- | --- | --- |
| Group | *Streptococcus mutans* | *Porphyromonas gingivalis* | *Fusobacterium nucleatum* subsp. *polymorphum* | *Aggregatibacter actinomycetemcomitans* |
| Blank control group | 0.00 | 0.00 | 0.00 | 0.00 |
| LAB single heat-inactivated liquid culture EG1 | 46.17 | 43.55 | 76.38 | 25.04 |
| LAB single heat-inactivated liquid culture EG2 | 42.94 | 70.33 | 40.80 | 20.47 |
| LAB single heat-inactivated liquid culture CG1 | 12.93 | 15.05 | 11.66 | 14.75 |
| LAB single heat-inactivated liquid culture CG2 | 9.54 | 9.99 | 21.56 | 17.77 |
| LAB heat-inactivated liquid culture mixture EG1 | 47.55 | 56.23 | 62.94 | 29.57 |
| LAB heat-inactivated liquid culture mixture EG2 | 57.13 | 76.13 | 78.12 | 30.66 |
| LAB heat-inactivated liquid culture mixture EG3 | 75.16 | 81.23 | 81.64 | 51.23 |

TABLE 11-continued

| Group | Growth inhibition percentage (%) | | | |
|---|---|---|---|---|
| | Streptococcus mutans | Porphyromonas gingivalis | Fusobacterium nucleatum subsp. polymorphum | Aggregatibacter actinomycetemcomitans |
| LAB heat-inactivated liquid culture mixture EG4 | 56.14 | 74.55 | 71.82 | 34.22 |
| LAB heat-inactivated liquid culture mixture EG5 | 51.56 | 54.55 | 61.06 | 30.29 |

As shown in Table 11, each of the LAB single heat-inactivated liquid culture EG1 and EG2 and the LAB heat-inactivated liquid culture mixture EG1 to EG5 exhibited a significant growth inhibitory effect on each of the oral pathogenic bacterial strains, and the percentage of growth inhibition exhibited by each of the LAB single heat-inactivated liquid culture EG1 and EG2 was significantly higher compared with that of the LAB single heat-inactivated liquid culture CG1 and CG2. These results indicate that the heat-inactivated liquid culture of *Lactobacillus rhamnosus* MP108 and the heat-inactivated liquid culture *Lactobacillus paracasei* MP137 are capable of effectively inhibiting the growth of oral pathogenic bacteria, and such inhibitory effect is significantly greater that those shown by different isolates of the same LAB species (i.e., *Lactobacillus rhamnosus* L-68 and *Lactobacillus paracasei* L-30).

In addition, in comparison with the LAB single heat-inactivated liquid culture EG1 and EG2, the LAB heat-inactivated liquid culture mixture EG2 to EG4 generally showed a trend of increase in growth inhibition percentage. In particular, the LAB heat-inactivated liquid culture mixture EG3 showed a most significant increase in growth inhibition percentage. These results suggest that, the heat-inactivated liquid culture of *Lactobacillus rhamnosus* MP108 and the heat-inactivated liquid culture of *Lactobacillus paracasei* MP137, when mixed in a specified volume ratio, exhibit a synergistic effect in inhibiting the growth of oral pathogenic bacteria.

In summary, regarding *Lactobacillus rhamnosus* MP108 and *Lactobacillus paracasei* MP137, their liquid cultures, heat-inactivated liquid cultures, or cell culture supernatants that are substantially free of bacterial cells all have an excellent inhibitory effect on the growth of oral pathogenic bacteria, which can be further enhanced when these LAB strains are mixed under a specific ratio range. Hence, these strains are expected to be useful for alleviating oral pathogenic bacteria-associated disorders.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for inhibiting growth of oral pathogenic bacteria, comprising applying a composition including liquid cultures of *Lactobacillus rhamnosus* MP108 and *Lactobacillus paracasei* MP137, which are deposited at the China General Microbiological Culture Collection Center (CGMCC) under accession numbers CGMCC 21225 and CGMCC 21224, respectively,
    wherein the liquid cultures are substantially free of bacterial cells, and a volume ratio of the liquid cultures of *Lactobacillus rhamnosus* MP108 and *Lactobacillus paracasei* MP137 in the composition ranges from 1:0.43 to 1:2.33.

2. The method as claimed in claim 1, wherein the liquid cultures are heat-inactivated.

3. The method as claimed in claim 1, wherein the oral pathogenic bacteria are selected from the group consisting of *Streptococcus mutans*, *Porphyromonas gingivalis*, *Fusobacterium nucleatum* subsp. *polymorphum*, *Aggregatibacter actinomycetemcomitans*, *Treponema denticola*, *Prevotella intermedia*, *Parvimonas micra*, *Campylobacter rectus*, *Eikenella corrodens*, and combinations thereof.

4. The method as claimed in claim 1, wherein the composition is formulated as a food product, a pharmaceutical composition or an oral hygiene composition.

5. A method for alleviating an oral pathogenic bacteria-associated disorder, comprising administering to a subject in need thereof a composition including liquid cultures of *Lactobacillus rhamnosus* MP108 and *Lactobacillus paracasei* MP137, which are deposited at the China General Microbiological Culture Collection Center (CGMCC) under accession numbers CGMCC 21225 and CGMCC 21224, respectively,
    wherein the liquid cultures are substantially free of bacterial cells, and a volume ratio of the liquid cultures of *Lactobacillus rhamnosus* MP108 and *Lactobacillus paracasei* MP137 in the composition ranges from 1:0.43 to 1:2.33.

6. The method as claimed in claim 5, wherein the liquid cultures are heat-inactivated.

7. The method as claimed in claim 5, wherein the oral pathogenic bacteria are selected from the group consisting of *Streptococcus mutans, Porphyromonas gingivalis, Fusobacterium nucleatum* subsp. *polymorphum, Aggregatibacter actinomycetemcomitans, Treponema denticola, Prevotella intermedia, Parvimonas micra, Campylobacter rectus, Eikenella corrodens*, and combinations thereof.

8. The method as claimed in claim 5, wherein the composition is formulated as a food product, a pharmaceutical composition or an oral hygiene composition.

* * * * *